United States Patent [19]

Small

[11] Patent Number: 4,960,944

[45] Date of Patent: Oct. 2, 1990

[54] TETRALIN OXIDATION

[75] Inventor: Robert J. Small, Satsuma, Ala.

[73] Assignee: Wesley II Limited Partnership, Montrose, Ala.

[21] Appl. No.: 381,869

[22] Filed: Jul. 19, 1989

[51] Int. Cl.$^5$ .............................................. C07C 45/34
[52] U.S. Cl. ..................................... 568/321; 568/311
[58] Field of Search ................................ 568/321, 311

[56] References Cited

U.S. PATENT DOCUMENTS

| | | | |
|---|---|---|---|
| 1,789,924 | 1/1931 | Benapfl et al. | 568/321 |
| 2,462,103 | 6/1949 | Johnson | 568/321 |
| 2,526,859 | 10/1950 | Foreman et al. | 568/321 |
| 2,588,359 | 3/1952 | Chitwood et al. | 568/321 |
| 3,340,311 | 9/1967 | Chitwood et al. | 568/321 |
| 3,354,231 | 11/1967 | Malor et al. | 568/321 |
| 3,395,183 | 7/1968 | Fenton | 568/321 |
| 4,283,352 | 8/1981 | Yamauchi et al. | 568/321 |
| 4,473,711 | 9/1984 | Coon | 568/321 |
| 4,753,911 | 6/1988 | Goe et al. | 568/321 |

FOREIGN PATENT DOCUMENTS 825480  4/1981  U.S.S.R. ............................ 568/321

*Primary Examiner*—James H. Reamer
*Attorney, Agent, or Firm*—Cushman, Darby & Cushman

[57] ABSTRACT

1-tetralone, an intermediate in the preparation of insecticides as well as agricultural chemicals and drugs, is prepared by the liquid-phase oxidation of tetralin in the presence of a copper compound, e.g. an oxide or hydroxide, having low or no organic solubility and limited water solubility, optionally, in conjunction with an inorganic iron compound and/or hydrogen peroxide.

15 Claims, No Drawings

TETRALIN OXIDATION

This invention relates in general to an improved liquid-phase process for the oxidation of tetralin to tetralone. In one aspect, this invention is directed to the oxidation of tetralin in the presence of an insoluble copper catalyst. In a further aspect, the invention relates to the oxidation of tetralin which utilizes an iron salt and/or hydrogen peroxide in the presence of an insoluble copper catalyst. In still another aspect, this invention relates to a one-step continuous process for the oxidation of tetralin to tetralone in the presence of an insoluble copper catalyst.

BACKGROUND OF THE INVENTION

Prior to the present invention a variety of homogeneous and heterogeneous catalysts have been reported in the literature for oxidation of various organic compounds including tetralin with gaseous oxygen. Many of the known catalyst systems have various problems with respect to reactant conversion, product yield, catalyst and product recovery, and the like, which have prevented many of these processes from becoming commercially successful.

One such reaction involves the oxidation of 1,2,3,4-tetrahydronaphthalene to 1(2H)naphthalenone, which is commonly referred to as "1-tetralone". Sizeable amounts of 1-tetralone are produced in the United States each year for use as an intermediate in the manufacture of insecticides as well as in the manufacture of other agricultural chemicals and drugs. Typically, 1-tetralone has been prepared by the liquid phase oxidation of tetralin in the presence of a homogeneous oxidation catalyst, with and without catalyst modifiers to improve reaction selectivity to 1-tetralone.

A fundamental problem with these homogeneous oxidation catalyst processes has been the relative difficulty in isolating the desired 1-tetralone or other products from the reaction mixture, regardless of selectivity. Not only must the undesired reaction by-products be separated from the desired product, but the homogeneous oxidation catalyst and homogeneous catalyst modifiers, if used, also must be separated out and recovered for subsequent reuse. As a result, the isolation of desired product, such as 1-tetralone, has historically required additional time-consuming distillation and other processing procedures thereby increasing production and other costs.

It is also known to use heterogeneous oxidation catalyst systems for the production of a 1-tetralone from tetralin. However, in many of these catalyst systems the selectivity of 1-tetralone is poor. Also, some of these catalysts are fine powders which can lead to plugging problems in the reactor. Good agitation is needed for the catalyst to be available in the entire reaction zone and hence, packed beds are not very suitable for the gas-liquid reactions. Also, some of these processes use homogeneous catalyst modifiers which require multistep separation still involving difficult and costly distillation procedures to remove the homogeneous modifier.

In contrast, most of the difficulties and disadvantages of the known methods have been overcome by the present invention. The novel insoluble catalyst compositions and process for using same, as disclosed herein, solve these fundamental problems found in prior art whole-or part-homogeneous catalyst systems for the oxidation of tetralin. The instant catalysts provide considerable advantages over the multi-part catalyst and modifier combinations. The need for a separate homogeneous modifier and the attendant additional processing and recovery steps are eliminated.

Accordingly, an object of this invention is to provide an improved liquid-phase process for the oxidation of tetralin to tetralone.

Another object of this invention is to provide an improved process for oxidation of tetralin in the presence of an insoluble catalyst.

A further object is to provide an improved process for the oxidation of tetralin which achieves high conversion rates and thereby permitting the use of a small continuous oxidation reaction zone.

Another object of this invention is to provide a process for the oxidation of tetralin wherein substantially no waste or by-product streams are produced.

Other objects, aspects, as well as the several advantages of the invention will be apparent to those skilled in the art upon reading the specification and appended claims.

SUMMARY OF THE INVENTION

In accordance with the invention, a process for the oxidation of tetralin to 1-tetralone is provided which comprises effecting the oxidation of tetralin in the presence of a catalyst comprising a copper compound having low or substantially no organic solubility and limited water solubility. Copper oxide and copper hydroxide are illustrative of such copper compounds. The copper catalyst of the invention can be readily separated, for example, by filtration, from the reaction mass.

In accordance with another embodiment, the oxidation of tetralin is carried out in the presence of a catalyst comprising a copper compound having low organic solubility and limited water solubility and an inorganic iron compound. The presence of the inorganic iron compound promotes decomposition of tetralin hydroperoxide into peroxy and hydroxy radicals that can either rearrange into the desired 1-tetralone product or further the oxidation process.

In still another embodiment of the invention, hydrogen peroxide is added to the oxidation reaction alone or in conjunction with the inorganic iron compound to initially form hydroxy radicals.

DETAILED DESCRIPTION OF THE INVENTION

In its broad aspect the invention relates to a process for the oxidation of tetralin to 1-tetralone by effecting the oxidation in the presence of a copper compound having low or no organic solubility and limited water solubility, optionally, in conjunction with an inorganic iron compound and/or hydrogen peroxide.

Thus, the present invention uses a copper compound, such as copper oxide and copper hydroxide, which performs as a one-part substantially insoluble oxidation catalyst for the oxidation of tetralin. Other copper compounds suitable that can be used include basic copper carbonate, copper ferrocyanide, basic copper sulfate and copper phosphate. The copper compounds should be organic insoluble but can have limited water solubility. The copper catalyst can be used as a slurry or as a fixed bed in the reaction mixture in continuous or batch equipment. A major advantage of this catalyst is that the metal catalyst is not removed with the product but held in the reactor for continuous use, thus reducing catalyst cost and the cost of additional product separations. If the catalyst does exit the reaction zone along with the reaction mass it can be readily separated by filtration or other suitable separation means.

The copper compounds employed in this invention can be employed in any desirable solid form readily available. The copper compound can be used as gauze in a trickle-bed or other fixed bed operation or as particulate material as in a slurry contact system or any other form as beads, bars, wire, etc.

As previously indicated, the copper catalyst of the invention can be used in conjunction with an inorganic iron compound and/or hydrogen peroxide to promote the oxidation reaction of tetralin to the desired 1-tetralone product. Suitable iron compounds that can be used include ferric or ferrous halides, hydroxides, oxides, phosphates, and sulfates, and the like, and mixtures thereof. Presently preferred are ferric chloride and ferrous chloride.

The copper compounds and iron compounds that can be used according to the invention are readily available commercially or can be prepared from commercially available materials.

The amount of copper and iron compounds used will be a catalytically effective amount sufficient to promote the oxidation reaction. Generally, the amount of copper compound used according to the invention ranges from about 0.1% to about 10% by weight as metal based upon tetralin in the reaction mixture. Similarly, the amount of iron compound, when present, will range from about 0.1% to about 10% by weight metal based upon the tetralin in the reaction mixture. The ratio of copper to iron will ordinarily be about 1.5:1 to 25:1.

The amount of hydrogen peroxide present when used will be an amount sufficient to cause formation of reactive species. Hydrogen peroxide in conjunction with certain initial salts (iron, copper, osmium, tungsten, and titanaium (as examples) will form reactive species including hydroxyl free radicals (.OH). These hydroxyl free radicals can react with organic materials to form oxygen containing products (alcohols, ketones, hydroperoxide, etc). Ordinarily, the amount, based upon tetralin, will be about 0.05 to about 5%.

N solvents are not mandatory in addition to the reactants and catalysts and the liquid-phase oxidation of tetralin can be carried out neat or in a suitable reaction diluent. Suitable specific diluents that have been used include 2-methyl-2-propanol, N-N-dimethyl formamide and toluene. Suitable diluents that will dissolve tetralin and its oxidation products can be used include aromatic solvents:

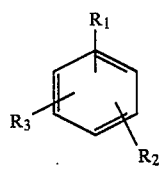

where $R_1$, $R_2$, and $R_3$ are any combination of H—, $CH_3$—, $CH_3CH_2$—$(CH_3)_3C$— groups though other groups could be used if economically feasible.

alcohols: 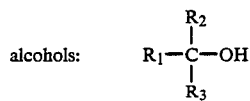

such as primary alcohols ($R_2$ and $R_3$=H and $R_1$=any alkyl group) or teretiary alcohols ($R_1$$R_2$ and $R_3$=any alkyl group).

Secondary alcohols can be used ($R_2$=H and $R_1$ and $R_3$=any alkyl group) but are more prone to decomposition from oxygen.

Amides can include

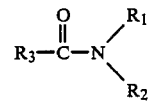

$R^1$, $R_2$ and $R_3$ equal to hydrogen or alkyl groups in any combination that is economically feasible.

Solvents or diluents not recommended are ethers ($R_1$—O—$R_2$; $R_1$ and $R_2 \neq H$ but=alkyl groups) since these systems are very susceptible to peroxide formation.

Gaseous oxygen as either pure molecular oxygen, air or an oxygen containing gas is used as oxidant. The amount of oxygen present during oxidation is a stoichiometric quantity which will achieve a 25-35% tetralin conversion and at the same time minimize the possibility of an uncontrolled oxidation reaction. The gaseous oxygen to tetralin should be high enough to enable the desired extent of reaction, but should not be sufficiently high to create a safety hazard. Oxygen pressures should be between about 50 to about 300 psig and preferably 100 to 200 psig.

The combination of catalyst and oxygen present during the oxidation process of the invention allows one to use a continuous liquid phase reaction to achieve 25-35% tetralin conversion in say 45-90 minutes instead of the traditional batch reactors requiring 600 minutes and longer. Only small quantities of tetralin hydroperoxide are present at any moment in the present process because of its rapid formation and rearrangement. The presence of large quantities of the hydroperoxide can be a safety hazard.

The temperature of the reaction is sufficiently elevated to cause oxidation to proceed at a desirable rate but not so high as to require significant heating and cooling equipment. Generally, the temperature of the process can range from about 80° to about 120° C., with from about 90° to about 115° C. being preferred.

The total pressure of the system should be sufficient to maintain liquid phase conditions. The oxygen partial pressure at the point of admixture with the liquid reactants is from about 50 psig to about 300 psig. Sufficient oxygen should be provided so that the reaction mixture is not oxygen starved to obtain the 25-35% conversion.

The reaction time for liquid phase, in a continuous mode of operation varies from about 30 to about 120 minutes depending upon the temperature and oxygen partial pressure. The contact time of gaseous oxygen with liquid can vary from about 1 to about 60 seconds depending on temperature and mixing effect.

The reaction type, i.e. batch, semi-continuous or continuous, is preferably continuous. The reaction can be carried out in any type of reaction zone giving good gas-liquid contact with the catalyst. One example of continuous reaction that has been used is the trickle bed process although other types of continuous reaction systems can be used.

For the purposes of further promoting a better understanding of the catalysts and process of the present invention, reference now will be made in the examples below to specific instances of their preparation and use. The following examples illustrate the best mode presently contemplated for the practice of the invention.

EXAMPLE 1

Effect of copper and $O_2$ pressure

Tetralin (50 ml) was charged into a 300 cc pressure reactor with 2-methyl-2-propanol (50 ml). N,N-dimethyl formamide (12.5 ml) and 3 g of copper hydroxide were stirred into the solution. The reactor was sealed and the oxygen pressure set at 200 psig with a 90° C. reaction temperature. The reaction was stopped after agitating (800 rpm) for ½ hr. The tetralin conversion was 39.5% and the 1-tetralone/1-tetralol ratio as 2.7 determined by gc methods.

EXAMPLE 2

Effect of copper and $O_2$ pressure.

Tetralin (50 ml) was charged into a 300 cc pressure reactor with 2 methyl-2-propanol (50 ml). N,N-Dimethyl acetamide (12.5) ml) and 3 g copper hydroxide were stirred into the solution. The reaction was sealed and the oxygen pressure set at 100 psig with a 80° C. reaction temperature. The reaction was stopped after agitating (800 rpm) for 1 ½ hr. The tetralin conversion was 44.8% and the 1-tetralone/1-tetralol ratio was 4 determined by gc methods.

EXAMPLE 3

Effect of $Fe^{III}$ and $H_2O_2$

Tetralin (50 ml) was charged into a 300 cc pressure reaction with 2 methyl-2 propanol (50 ml). N,N-dimethyl acetamide (13 ml)., 3 g iron chloride and copper hydroxide were stirred into the solution followed by five drops of 30% hydrogen peroxide. The reaction was sealed and the oxygen pressure set at 200 psig with a 90° C. reaction temperature. The reaction was stopped after agitating (800 rpm) for ½ hr. The tetralin conversion was 53.8% and the 1-tetralone/1-tetralol ratio was 6.3 by gc methods.

EXAMPLE 4

Effect of $Fe^{III}$ and $H_2O_2$

Tetralin (50 ml) was charged into a 300 cc pressure reactor with 2-methyl-2-propenol (50 ml). N,N dimethyl acetamide (12.5 ml), 3 g copper hydroxide, 0.25 g Iron chloride and 0.2 g of 30% hydrogen peroxide were added to the reactor. The reactor was sealed and the oxygen pressure was set at 200 psig with a 90° C. reaction temperature. The reaction was stopped after agitating (860 rpm) of ½ hr. The tetralin conversion was 48.9% and the 1-tetralone/1-tetralol ratio was 3.7.

EXAMPLE 5

Effect of $Fe^{III}$ and $H_2O_2$

Tetralin (50 ml) was charged into a 300 cc pressure reactor with 2-methyl-2 propanol (50 ml). N,N Diethyl acetamide (12.5 ml), 0.5 g iron (111) chloride and 3 g copper hydroxide were stirred into the solution followed by five drops of 30% hydrogen peroxide. The reaction was sealed and the oxygen pressure was set at 200 psig with a 90° C. reaction temperature. The tetralin conversion was 47.2% and the 1-tetralone/1-tetralol ratio was 4 by gc methods.

EXAMPLE 6

Continuous Oxidation

A 304 SS trickle-bed reactor (0.75" diameter and 36" long) with copper gauze was assembled with an oxygen and organic feed point. A diaphragm pump circulated a 200 ml tetralin charge through the packed column every 2 minutes. In certain runs additives were added with the tetralin.

| Run No | Additive | $O_2$ Press. | Temp. (°C.) | Time | Tetralin Conv. | One/ol |
|---|---|---|---|---|---|---|
| 1 | — | 50–65 | 103–100 | 120 | 24% | 2.1 |
| 2 | 1 wt % CU(OH)$_2$ | 53–70 | 103–106 | 150 | 26% | 2.1 |
| 3 | 0.5 wt % Cu(OH)$_2$ | 80–110 | 104–105 | 120 | 32.7 | 2.6 |
| 4 | 1.7 wt % $H_2O_2$ 1 wt % Cu(OH)$_2$ | 70–80 | 104–105 | 120 | 31.7 | 3.1 |

EXAMPLE 7

Tetralin Oxidation

A 45 cc 304 SS cylinder was charged with tetralin (2 g) and toluene (5 ml). Various catalysts (1 wt% of tetralin) were used for the oxidation reactions. The cylinder was sealed with 200 psig oxygen and shaken at 860 cpm in a 100° C. sand bath. The reaction was analyzed by GC after one hour. The one/ol ratio is the tetralone gc area % divided by 1-tetralol's.

| Catalyst | Area % | | | | |
|---|---|---|---|---|---|
| | Tetralin | 1-Tetralone | 1-Tetrelol | Conversion | one/ol |
| Cobalt neodecanoate (12%) | 62 | 24.6 | 12.7 | 36 | 2 |
| None | 81.3 | 10.3 | 5.1 | 16 | 2 |
| Copper Chem-All ® (30%) | 31.2 | 47.2 | 11.1 | 65 | 4.3 |
| Iron | 64.3 | 18.1 | 10.6 | 31 | 1.7 |

-continued

| Catalyst | Tetralin | 1-Tetralone | 1-Tetrelol | Conversion | one/ol |
|---|---|---|---|---|---|
| Naphthelate (6%) | | | | | |

EXAMPLE 8

Tetralin Oxidation

Tetralone (132 g), toluene (131 g), and 0.5 g of copper hydroxide suspension (37.5% $Cu(OH)_2$), were mixed into a 500 ml round bottom with temperature control, gas dispersion tube, water-cooled condenser and a magnetic stirrer. The reaction was maintained at 80° C. for 9.8 hr. with a 300 ml/minute oxygen flow at atmospheric pressure. GC analysis (area %) indicates 3% 1-tetralol, 5.2% 1-tetralone and 15% 1-tetralin hydroperoxide.

EXAMPLE 9

Oxidation with Various Catalysts

Tetralin (50 ml) was charged into a 300 cc pressure reactor with the appropriate catalyst quantity. The oxygen pressure was adjusted to 200 psig while the reaction temp was set at 90° C. The agitator was 800 rpm. The reaction was stopped after 1½ hr. The tetralin conversion (Tet. Con.) and the 1-tetralone/1-tetralol (one/$_{ol}$) ratio were determined by GC methods.

| | Solvent | Catalysts | (g) | Tet. Con | One/$_{ol}$ |
|---|---|---|---|---|---|
| •23 | toluene | Cu (OH)$_2$ | 3 g | 42% | 1.7 |
| •25 | toluene | Na$_2$CO$_3$ | 25 g | 30 | 1.3 |
| •18 | toluene | — | | 29 | 2.5 |

EXAMPLE 10

Continuous Oxidation

A 304 stainless steel trickle-bed reactor (1.50" diameter and 72" long) packed with ⅜" copper balls was assembled with a cooling/heating jacket and an oxygen and organic feed point. A centrifugal pump circulated a 600 milliter tetralin charge (with 1.5 grams of copper hydroxide) through the packed column once every 10 to 15 seconds. The oxygen pressure was maintained at 200 psig, and the reaction temperature was between 88° and 93° C. After 64 minutes, there was a 34% tetralin conversion with an ~3.6:1 one/$_{ol}$ ratio.

What is claimed is:

1. A process for the liquid-phase oxidation of tetralin to tetralone which comprises contacting tetralin under oxidation conditions with gaseous oxygen in the presence of a catalyst comprising copper hydroxide having low organic and water solubility.

2. A process according to claim 1 wherein the oxidation is carried out in the presence of an inorganic compound of iron.

3. A process according to claim 1 or claim 2 wherein said contacting is carried out in the presence of hydrogen peroxide ($H_2O_2$).

4. A process according to claim 1 wherein the reaction is carried out in an organic diluent and the organic diluent is selected from aromatic hydrocarbons, alcohols, and amides that will dissolve tetraline and its oxidation products.

5. A process according to claim 1 wherein said contacting is carried out at a temperature ranging from about 90° to about 120° C.

6. A process according to claim 4 wherein the oxidation is carried out in the presence of an inorganic iron compound.

7. A process according to claim 6 wherein said contacting is carried out in the presence of hydrogen peroxide.

8. A process according to claim 7 wherein said contacting is carried out at a temperature ranging from about 80° to about 120° C.

9. A continuous one-step process for the oxidation of tetralin to tetralone comprising passing tetralin, copper hydroxide and oxygen in an organic diluent through a fixed bed of copper under oxidation conditions.

10. A process according to claim 9 wherein said oxidation is carried out in a trickle-bed reaction zone packed with copper gauze.

11. A process according to claim 1 wherein the amount of oxygen present during oxidation is a stoichiometric quantity which will achieve a 25–35% tetralin conversion.

12. A process according to claim 4 wherein said organic diluent is selected from toluene, 2-methyl-2-propanol, N,N-dimethyl formamide, and N,N-dimethyl acetamide.

13. A process according to claim 2 wherein said iron compound is iron chloride and the ratio of copper to iron is about 1.5:1 to 25:1.

14. A process according to claim 13 wherein hydrogen peroxide is present in an amount, based on tetralin, from about 0.05 to about 5%.

15. A process according to claim 9 wherein the amount of oxygen present during oxidation is a stoichiometric quantity which will achieve a 25–35% tetralin conversion.

* * * * *